US00PP36897P2

(12) United States Plant Patent
Pieters

(10) Patent No.: US PP36,897 P2
(45) Date of Patent: Aug. 19, 2025

(54) ***CHRYSANTHEMUM* PLANT NAMED 'G24MAG14RE'**

(50) Latin Name: ***Chrysanthemum* x *morifolium***
Varietal Denomination: G24MAG14RE

(71) Applicant: PARATY B.V., Oostnieuwkerke (BE)

(72) Inventor: Elien Sofie Pieters, Oostnieuwkerke (BE)

(73) Assignee: PARATY B.V., Oostnieuwkerke (BE)

( * ) Notice: Subject to any disclaimer, the term of this patent is extended or adjusted under 35 U.S.C. 154(b) by 0 days.

(21) Appl. No.: 19/006,053

(22) Filed: Dec. 30, 2024

(51) Int. Cl.
*A01H 5/02* (2018.01)
*A01H 6/14* (2018.01)

(52) U.S. Cl.
USPC ..... Plt./293

(58) Field of Classification Search
USPC ..... Plt./293
See application file for complete search history.

*Primary Examiner* — Susan McCormick Ewoldt
(74) *Attorney, Agent, or Firm* — C. Anne Whealy

(57) ABSTRACT

A new and distinct cultivar of *Chrysanthemum* plant named 'G24MAG14RE', characterized by its upright, outwardly spreading and uniformly rounded plant habit; moderately vigorous growth habit; freely branching habit; dense and full plant habit; flexible stems; medium green-colored leaves; uniform and freely flowering habit; long flowering period; decorative-type inflorescences with ray florets that are dark red in color; and excellent garden performance.

1 Drawing Sheet

Botanical designation: *Chrysanthemum* x *morifolium*.
Cultivar denomination: 'G24MAG14RE'.

CROSS-REFERENCED TO CLOSELY-RELATED APPLICATION

Title: *Chrysanthemum* Plant Named 'G24MAG11OR'
Inventor: Elien Sofie Pieters
Filed: Concurrently with the instant application

BACKGROUND OF THE INVENTION

The present invention relates to a new and distinct cultivar of *Chrysanthemum* plant, botanically known as *Chrysanthemum* x *morifolium*, typically grown as a garden *Chrysanthemum* and hereinafter referred to by the name 'G24MAG14RE'.

The new *Chrysanthemum* plant is a product of a planned breeding program conducted by the Inventor in Oostnieuwkerke, Belgium. The objective of the breeding program is to create new uniformly mounding and freely flowering *Chrysanthemum* plants with unique and attractive inflorescence form and ray floret coloration.

The new *Chrysanthemum* plant is a naturally-occurring whole plant mutation of *Chrysanthemum* x *morifolium* 'G22MAG13BR', disclosed in U.S. Plant Pat. No. 33,666. The new *Chrysanthemum* plant was discovered and selected by the Inventor as a single flowering plant from within a population of plants of 'G22MAG13BR' grown in a controlled greenhouse environment in Oostnieuwkerke, Belgium in September, 2022.

Asexual reproduction of the new *Chrysanthemum* plant by vegetative terminal cuttings was first conducted in a controlled greenhouse environment in Oostnieuwkerke, Belgium in March, 2023. Asexual reproduction by vegetative terminal cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'G24MAG14RE'. These characteristics in combination distinguish 'G24MAG14RE' as a new and distinct *Chrysanthemum* plant:

1. Upright, outwardly spreading and uniformly rounded plant habit; moderately vigorous growth habit.
2. Freely branching habit; dense and full plant habit; flexible stems.
3. Medium green-colored leaves.
4. Uniform and freely flowering habit.
5. Long flowering period.
6. Decorative-type inflorescences with ray florets that are dark red in color.
7. Excellent garden performance.

Plants of the new *Chrysanthemum* can be compared to plants of the mutation parent, 'G22MAG13BR'. In side-by-side comparisons, plants of the new *Chrysanthemum* differ primarily from plants of 'G22MAG13BR' in ray floret color as inflorescences of the new *Chrysanthemum* have dark red-colored ray florets whereas inflorescences of plants of 'G22MAG13BR' have reddish bronze-colored ray florets. In addition, plants of the new *Chrysanthemum* are stronger and more vigorous than plants of 'G22MAG13BR'.

Plants of the new *Chrysanthemum* can be compared to plants of *Chrysanthemum* x *morifolium*, 'G24MAG11OR', disclosed in a U.S. Plant patent application Ser. No. 19/006,038, filed concurrently. In side-by-side comparisons, plants of the new *Chrysanthemum* differ primarily from plants of 'G24MAG11OR' in ray floret color as inflorescences of the new *Chrysanthemum* have dark red-colored ray florets whereas inflorescences of plants of 'G24MAG11ORE' have reddish orange-colored ray florets.

Plants of the new *Chrysanthemum* can also be compared to plants of *Chrysanthemum* x *morifolium* 'Magnus Violet', disclosed in U.S. Plant Pat. No. 23,964. In side-by-side comparisons, plants of the new *Chrysanthemum* differ primarily from plants of 'Magnus Violet' in ray floret color as inflorescences of plants of the new *Chrysanthemum* have dark red-colored ray florets whereas inflorescences of plants of 'Magnus Violet' have purple-colored ray florets.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. The photograph comprises a side perspective view of a typical flowering plant of 'G24MAG14RE' grown in a container.

DETAILED BOTANICAL DESCRIPTION

The aforementioned photograph and following observations and measurements describe plants grown in 19-cm containers in an outdoor nursery in Oostnieuwkerke, Belgium under natural daylengths and employing cultural practices typically used in commercial garden *Chrysanthemum* production. During the production of the plants, day temperatures ranged from 20° C. to 25° C. and night temperatures ranged from 12° C. to 18° C. Plants were 20 weeks old when the photograph and the detailed description were taken. In the following description, color references are made to The Royal Horticultural Society Colour Chart, 2015 Edition, except where general terms of ordinary dictionary significance are used.

Botanical classification: *Chrysanthemum* x *morifolium* 'G24MAG14RE'.

Parentage: Naturally-occurring whole plant mutation of *Chrysanthemum* x *morifolium* 'G22MAG13BR', disclosed in U.S. Plant Pat. No. 33,666.

Propagation:

- *Type cutting*.—By vegetative tip cuttings.
- *Time to initiate roots, summer*.—About 14 days at temperatures about 20° C.
- *Time to initiate roots, winter*.—About 20 days at temperatures about 20° C.
- *Time to produce a rooted young plant, summer*.—About 30 days at temperatures about 20° C.
- *Time to produce a rooted young plant, winter*.—About 40 days at temperatures about 20° C.
- *Root description*.—Fine, fibrous; typically light brown in color, actual color of the roots is dependent on substrate composition, water quality, fertilizer type and formulation, substrate temperature and physiological age of roots.
- *Rooting habit*.—Freely branching; medium density.

Plant description:

- *Appearance*.—Perennial decorative type *Chrysanthemum* with oblong-shaped ray florets; stems upright and outwardly spreading giving a uniformly rounded appearance to the plant; plants roughly spherical; very freely branching habit, about 25 to 30 primary lateral branches developing per plant, each primary lateral branch with multiple secondary branches; pinching is not required, but enhances lateral branch development; dense and full plant habit; moderately vigorous growth habit and moderate growth rate; plants flexible, not brittle.
- *Plant height*.—About 40 cm.
- *Plant width*.—About 50 cm.
- *Lateral branches*.—Length: About 25 cm. Diameter: About 2 mm to 3 mm. Internode length: About 2 cm. Strength: Moderately strong, flexible. Texture: Pubescent, fine; longitudinally ridged. Color: Close to 138A.
- *Leaves*.—Arrangement: Alternate, simple. Length: About 3 cm to 5 cm. Width: About 2.5 cm to 3 cm. Apex: Rounded to cuspidate. Base: Attenuate. Margin: Palmately lobed and serrate, sinuses between lateral lobes divergent to parallel. Texture, upper and lower surfaces: Slightly pubescent. Venation: Palmately reticulate. Color: Developing leaves, upper surface: Close to 137C. Developing leaves, lower surface: Close to 137D. Fully expanded leaves, upper surface: Close to N137C; venation, close to 148C. Fully expanded leaves, lower surface: Close to 147B; venation, close to 147B to 147C. Petioles: Length: About 1 cm. Diameter: About 2 mm. Texture, upper and lower surfaces: Slightly pubescent; slightly rough. Color, upper surface: Close to 146C. Color, lower surface: Close to 146D. Stipules: Length: About 1 cm. Diameter: About 2 mm. Texture, upper and lower surfaces: Slightly pubescent. Color, upper and lower surfaces: Close to 137A.

Inflorescence description:

- *Appearance*.—Decorative-type inflorescence form; inflorescences borne on terminals above foliar plane; disc and ray florets arranged acropetally on a capitulum.
- *Fragrance*.—Slightly fragrant, pungent.
- *Flowering response*.—Under natural season conditions, plants flower in mid-September in Belgium; flowering response time, about 35 days.
- *Postproduction longevity*.—Inflorescences maintain good color and substance for about six weeks; inflorescences persistent.
- *Quantity of inflorescences*.—About 30 to 35 inflorescences develop per lateral branch.
- *Inflorescence buds*.—Height: About 8 mm. Diameter: About 1.3 cm. Shape: Globular. Color: Close to 181A.
- *Inflorescence diameter*.—About 5 cm.
- *Inflorescence depth* (*height*).—About 3.5 cm.
- *Disc diameter*.—About 3 mm; inconspicuous.
- *Receptacle diameter*.—About 3 mm.
- *Receptacle height*.—About 2.5 mm to 3 mm.
- *Receptacle shape*.—Raised dome.
- *Receptacle color*.—Close to 144B.
- *Ray florets*.—Number of ray florets per inflorescence: About 150 to 200 arranged in about ten whorls. Length: About 3.5 cm to 5 cm. Width: About 7 mm. Shape: Oblong, flat. Apex: Rounded. Base: Attenuate. Margin: Entire. Aspect: Mostly horizontal. Texture and luster, upper and lower surfaces: Smooth, glabrous; matte. Color: When opening, upper surface: Close to 53A. When opening, lower surface:

Close to 180A. Fully opened, upper surface: Close to 53A; color becoming closer to 50A with subsequent development. Fully opened, lower surface: Close to 181B; color becoming closer to 47B with subsequent development.

*Disc florets*.—Number of disc florets per inflorescence: About 20 massed at the center of the inflorescence; inconspicuous. Length: About 3 mm. Diameter: About 0.5 mm to 1 mm. Shape: Tubular; apices dentate. Texture and luster: Smooth, glabrous; glossy. Color, immature: Close to 145A. Color, mature: Close to 12A.

*Phyllaries*.—Number of phyllaries per inflorescence: About 25 arranged in about two or three whorls. Length: About 4 mm to 6 mm. Width: About 2 mm to 3 mm. Shape: Ovate. Apex: Rounded. Base: Rounded to truncate. Margin: Entire; translucent. Texture, upper and lower surfaces: Smooth, glabrous. Color, upper surface: Close to 137A. Color, lower surface: Close to N137B.

*Peduncles*.—Length, terminal peduncle: About 5 cm. Length, fourth peduncle: About 5 cm. Length, seventh peduncle: About 5 cm. Diameter: About 2 mm. Angle: About 30° from vertical. Strength: Moderately strong. Texture: Slightly pubescent. Color: Close to 138A.

*Reproductive organs*.—Androecium: Stamen development has not been observed on inflorescences of the new *Chrysanthemum*. Gynoecium: Pistil development has not been observed on inflorescences of the new *Chrysanthemum*.

*Seeds and fruits*.—To date, seed and fruit production have not been observed on plants of the new *Chrysanthemum*.

Garden performance: Plants of the new *Chrysanthemum* have demonstrated excellent garden performance and will tolerate temperatures ranging from about 1° C. to about 45° C.

It is claimed:

1. A new and distinct *Chrysanthemum* plant named 'G24MAG14RE' as herein illustrated and described.

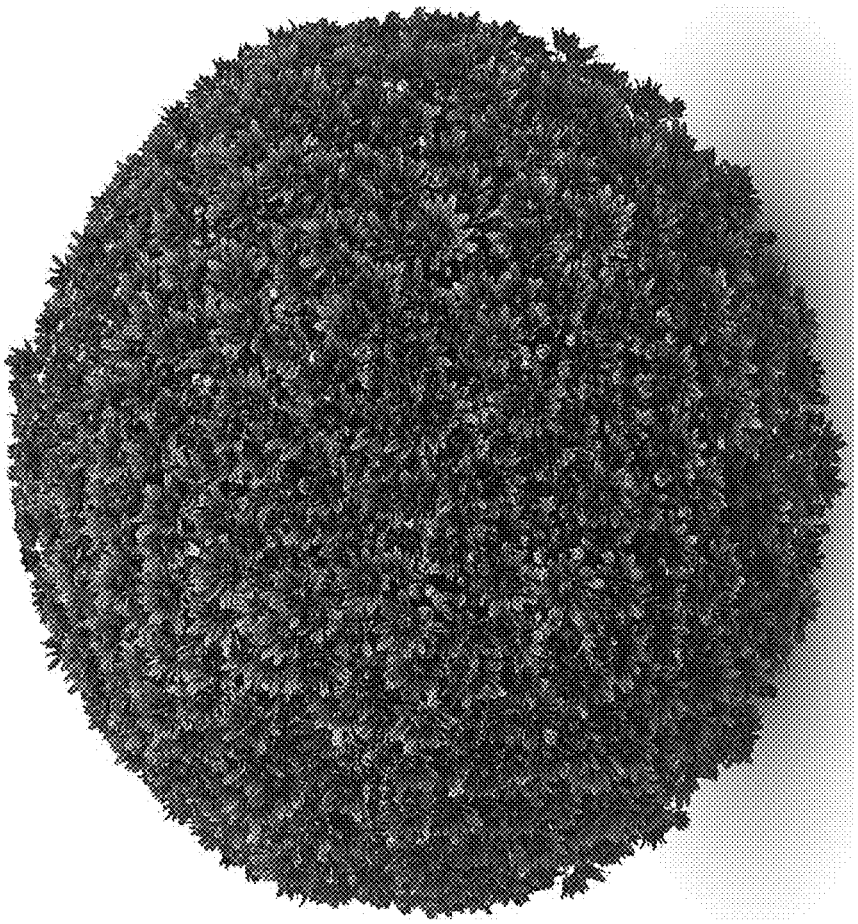

* * * * *